United States Patent [19]

Longiaru et al.

[11] Patent Number: 5,232,829

[45] Date of Patent: Aug. 3, 1993

[54] DETECTION OF CHLAMYDIA TRACHOMATIS BY POLYMERASE CHAIN REACTION USING BIOTIN LABELLED LINA PRIMERS AND CAPTURE PROBES

[75] Inventors: Mathew Longiaru, West Orange; Sheryl B. Silver, Fort Lee, both of N.J.; Michael A. Sulzinski, Spring Valley, N.Y.

[73] Assignee: Hoffmann-La Roche Inc., Nutley, N.J.

[21] Appl. No.: 414,542

[22] Filed: Sep. 29, 1989

[51] Int. Cl.$^5$ .................. C12Q 1/68; C12Q 1/02; C12Q 1/16; C07H 15/12

[52] U.S. Cl. .................................. 435/6; 435/29; 435/34; 435/35; 536/24.32; 536/24.33; 935/2; 935/16; 935/19

[58] Field of Search ................ 435/6, 7; 422/56

[56] References Cited

U.S. PATENT DOCUMENTS

| | | | |
|---|---|---|---|
| 4,154,795 | 5/1979 | Thorne | 422/99 |
| 4,228,237 | 10/1980 | Hevey et al. | |
| 4,358,535 | 11/1982 | Falkow et al. | |
| 4,486,539 | 12/1984 | Ranki et al. | |
| 4,683,195 | 7/1987 | Mullis et al. | |
| 4,683,202 | 7/1987 | Mullis | |
| 4,725,388 | 2/1988 | Nelson et al. | |
| 4,731,325 | 3/1988 | Palva et al. | |
| 4,751,177 | 6/1988 | Stabinsky | |
| 4,797,355 | 1/1989 | Stabinsky | |
| 4,822,731 | 4/1989 | Watson et al. | |

FOREIGN PATENT DOCUMENTS

| | | |
|---|---|---|
| 237362 | 9/1987 | European Pat. Off. |
| 302715 | 2/1989 | European Pat. Off. |
| 336412 | 10/1989 | European Pat. Off. |
| 439222 | 7/1991 | European Pat. Off. |
| 8706621 | 11/1987 | PCT Int'l Appl. |
| 2139349A | 11/1984 | United Kingdom |
| 2187283A | 9/1987 | United Kingdom |
| 2202328 | 9/1988 | United Kingdom |
| 83/01459 | 4/1983 | World Int. Prop. O. |
| 05815 | 10/1986 | World Int. Prop. O. |
| 87/06621 | 11/1987 | World Int. Prop. O. |
| 89/11548 | 11/1989 | World Int. Prop. O. |

OTHER PUBLICATIONS

Dahlen et al., Molecular and Cellular Probes, 1:159-168 (1987).
Langdale et al., Gene 36:201-210 (1985).
Polsky-Cynkin et al., Clin. Chem. 31:1438-1443.
Sylvanen et al., Nucleic Acids Res. 16:11327-11338 (1988).
Sylvanen et al., Nucleic Acids Res. 14:5037-5048 (1986).
Keller et al., Anal. Biochem. 177:27-32 (1989).
Keller et al., J. Clin. Microbiol. 28:1411-1416 (1990).
Sakai, Proc. Natl. Acad. Sci. U.S.A. 86:6230-6234 (1989).
Sriprakash et al., Plasmid 18:205-214 (1987).
Pollard et al., Molecular and Cellular Probes 3:383-389 (1989).
Running et al., BioTechniques, vol. 8, No. 3, pp. 276-277 (1990).
Nicholls et al., J. Clin. Lab. Anal. 3:122-135 (1989).
Urdea et al., Clin. Chem. 35:1571-1575 (1989).
Urdea et al., Gene 61:253-264 (1987).
Urdea et al., Nucleic Acids Res. 16:4937-4955 (1988).
Keller et al., J. Clin. Microbiol. 29:638-641 (1991).

(List continued on next page.)

*Primary Examiner*—Robert A. Wax
*Assistant Examiner*—Miguel T. Escallon
*Attorney, Agent, or Firm*—George M. Gould; William H. Epstein; John J. Schlager

[57] ABSTRACT

The present invention relates to the synthesis of amplified biotin-labelled DNA target sequences of *Chlamydia trachomatis* by polymerase chain reaction techniques and the detection of such sequences by a microtiter plate having plurality of wells and having bound thereto oligonucleotide capture probe complementary to said target sequence.

16 Claims, 3 Drawing Sheets

OTHER PUBLICATIONS

Cook et al., Nucleic Acids Research, vol. 16, No. 9, pp. 4077–4095 (1988).

Ghosh et al., Nucleic Acids Research, vol. 15, No. 13, pp. 5353–5372 (1987).

Gingeras et al., Nucleic Acids Research, vol. 15, No. 13, pp. 5373–5390 (1987).

Nagata et al., Fed. European Biochem. Soc., vol. 183, No. 2, pp. 379–382 (1985).

Chirgwin et al., Am. Chem. Soc., vol. 18, No. 24, pp. 5294–5290 (1979).

Cheley et al., Analytical Biochem., vol. 137, pp. 15–19 (1984).

Firestein et al., Analytical Biochem., vol. 167, pp. 381–386 (1987).

Thompson et al., Analytical Biochem., vol. 163, pp. 281–291 (1987).

Pellegrino et al., BioTechniques, vol. 5, No. 5, pp. 452–459 (1987).

Cook et al. (1988) Synthesis and Hybridization of a Series of Biotinylated Oligonucleotides Nucl. Acid Res 16(9):4027.

Pellegrino et al. (1987) A Sensitive Solution Hybridization Technique for Detection of RNA in Cells. Biotechniques, 5:45 2–59.

Firestein et al. (1987) Quantitative Molec Hybridization using RNA Probes and Page Anal. Biochem 167:381–386.

Chirquin et al. (1979) Isolation of Biologically Active RNA from Enriched Ribonase Biochem 18(24) 5294.

Thomson and Gillespie (1987) Molecular Hybirdization with RNA Probes in Concentrate Guanidine Thiocyanate Anal. Biochem 163:281.

Hatt et al. (1988) Analysis of the Entire Nucleotide Sequence of Plasmid Chlamydia Trachomatis. Serovar L1: Nucl. Acid Res. 16(9) 4053.

DETECTION OF CHLAMYDIA TRACHOMATIS BY POLYMERASE CHAIN REACTION USING BIOTIN LABELLED LINA PRIMERS AND CAPTURE PROBES

BACKGROUND OF THE INVENTION

1. Technical Field

The present invention relates to the field of nucleic acids and in particular to detection methods relating thereto. It further relates to the diagnosis of various infectious diseases by such detection. It further relates to the synthesis of amplified biotin-labelled DNA sequences by polymerase chain reaction techniques, and the detection of such sequences by microtiter plate capture. It still further relates to novel primers and capture probes that are capable of detecting *Chlamydia trachomatis*.

2. Description of Related Disclosures

U.S. Pat. Nos. 4,683,195 and 4,683,202 (both incorporated herein by reference) disclose methods of amplifying DNA sequences by a technique now known in the art as "polymerase chain reaction" (PCR). The polymerase chain reaction is a procedure in which DNA is specifically amplified by multiple primer extension syntheses of complementary strands (Saiki et al, Science, 230: 1350–1354 and 239: 489–491; 1985, 1988). The PCR product, amplified up to $10^6$–$10^7$ fold, is a DNA fragment of discrete size (amplicon) which can be detected by gel electrophoresis, or by other means as described herein. Briefly, PCR involves the preparation of short oligonucleotide primers which correspond to opposing ends of a known "target" sequence which one intends to amplify and subsequently detect. In this Procedure, DNA or RNA is extracted from cells, tissues, body fluids and the like. The nucleic acid is denatured and the oligonucleotide primers are added in molar excess, along with dNTPs (deoxyribonucleotide triphosphates) and a DNA polymerase enzyme, such as preferably heat stable Tao polymerase. Upon subsequent heat denaturing, cooling to allow annealing to primers, and primer extension by DNA Polymerase, two "long products", which begin with the respective primers, are produced, complementary to the two original strands. This procedure is repeated, and after a second cycle two original strands, two long products from cycle 1, two new "long products", and two "short products" are produced. The length of these short products (amplicons) is equal to the number of nucleotides between and including both primers. With additional cycles, additional "long products" are produced, increasing in a linear fashion with each cycle. However, the generation of amplicons increases at an exponential rate with each cycle, and by means of this amplification, the detection of extremely small quantities of DNA is enabled.

Through the use of PCR technology, the detection of specific DNA sequences present in minute quantities is possible. Several of these techniques involve the use of various hybridized probes affixed to certain materials.

As will be fully described later, the present invention utilizes fixation of a capture DNA sequence to microtiter wells and subsequent detection by hybridization to labelled (viz. biotinylated) amplicons. It also involves the use of guanidine thiocyanate in the hybridization step. Several procedures have been described in the literature which are relevant herein. Two such reports describe the immobilization of large target DNAs to microtiter wells, followed by the hybridization of these targets to biotinylated oligonucleotide or nick-translated DNA probes.

Cook et al., *Nucleic Acids Research*, 16:4077–4095 (1988) immobilized bacteriophage M13 target DNA on microtiter wells of Immulon2 plates by incubating target DNA in 1 M ammonium acetate for 1.5–2 hours at 37° C. The immobilized target DNA was detected after hybridization to terminal-biotin labelled or internal-biotin labelled oligonucleotide probes, followed by addition of streptavidin-HRP complex and hydrogen peroxide/o-phenylene diamine (OPD) for colorimetric detection of hybridization.

Nagata et al., *FEBS Lett.*, 183:379–382 (1985) immobilized lambda target DNA in microtiter wells in PBS containing 0.1 M $MgCl_2$. After an overnight room temperature incubation followed by removal of the solution, the plate was irradiated with ultraviolet light. Hybridization with a biotinylated (nick-translated) lambda DNA probe was followed by complexing with avidin-betagalactosidase. Fluorescence was measured after the addition of the substrate, 4-methylumbelliferyl-beta-D-galactoside.

Hevey et al., U.S. Pat. No. 4,228,237, described a method which uses biotin reacting to avidin (covalently attached to an enzyme) to detect a ligand in liquid medium. Our present method differs in that the ligand is directly labelled with biotin, not an intermediate biotin labelled anti-ligand. Further, various other prior disclosures describe specific hybridization probes and diagnostic uses thereof; e.g., U.S. Pat. No. 4,358,535 issued to Falkow and EP 63,879 to Ward. The latter describes the use of biotin-labelled DNA probes detected by enzymes linked to avidin or biotin-specific antibodies.

Ranki et al., U.S. Pat. No. 4,486,539, describes the use of two non-overlapping nucleic acid reagents (one bound to a solid carrier and the other being labelled) to detect and identify microbes by DNA hybridization. The present invention differs in that the target nucleic acid is itself labelled, and does not require the use of an additional labelled nucleic acid probe for detection.

Stabinsky, U.S. Pat. No. 4,751,177, described a DNA detection method wherein the target DNA is hybridized in solution to a mediator polynucleotide and to a labelled probe polynucleotide. The mediator polynucleotide, in turn, is complementary to a polynucleotide immobilized on a solid support. The present invention differs in that (a) the target is labelled during amplification; no labelled reporter group is needed for detection, and (b) the capture probe is bound directly to a solid support, without the use of a mediator polynucleotide.

Guanadine thiocyanate (GuSCN) has been used in cell extraction and subsequent nucleic acid hybridization. For example, Thompson and Gillespie, *Anal. Biochem.*, 163:281–291 (1987), prepared radiolabelled RNA probes to detect target DNA or RNA. In a dot blot format, the $^{32}$P-labelled probe was hybridized in 5 M GuSCN/0.1 M ethylenediaminetetraacetic acid (EDTA), disodium salt, pH 8.0. Pellegrino et al., *Biotechniques*, 452–459 (1987), described a solution hybridization to detect HIV-RNA in blood cells. Blood cells were dissolved in 5 M GuSCN/0.1 M EDTA and hybridized with a radiolabelled RNA probe in the same solution at room temperature. TCA-precipitated hybrids were collected on membranes and radioactivity was determined by scintillation counting. Gillespie, International Patent Application #PCT/US87/01023, (1987), described the use of guanidine thiocyanate for molecular hybridization using a labelled probe to detect target DNA bound to a solid support. The patent describes the use of GuSCN for molecular hybridization over a concentration range of 3 M-6.5 M at ambient temperature. The format for such hybridization includes binding target nucleic acid to nitrocellulose or nylon membrane (dot blot or Southern blot), prehybridization, hybridization to a radiolabelled Probe in GuSCN, washing and detection by autoradiography.

SUMMARY OF THE INVENTION

That is provided herein a format for hybridization capture of polymerase chain reaction (PCR) amplified DNA on a polystyrene solid support having enhanced protein binding capacity. Preferably such solid support is a microtiter plate having a plurality of wells. After labelling the amplified target DNA (e.g., with biotin) during amplification in the PCR reaction, the labelled DNA is specifically captured by base-pair hybridization to an amplicon-specific oligonucleotide capture probe that has been passively bound to the microtiter well. If biotin is used as the label, avidin:HRP complex is added and is reacted with either (a) hydrogen peroxide substrate and o-phenylene diamine (OPD) chromogen or (b) hydrogen peroxide substrate and tetramethylbenzidine chromogen (TMB). A colorimetric signal develops, allowing for the quantitative detection of PCR-amplified DNA.

The sensitivity of the plate capture of biotinylated PCR products has been found to be comparable to the sensitivity using radiolabelled probes in Southern blot hybridizations and oligonucleotide hybridization (OH) assays. The plate capture format, however, offers several advantages: (a) quicker assay time; (b) a less labor intensive assay format, without the use of a radiolabelled probe and (c) an objective, quantitative evaluation of hybridization.

Another aspect of the invention is the diagnosis of specific disease states by the detection of the presence of specific DNA sequences that characterize the causative microorganism. Specific probes and primers have been discovered for one of such microorganisms; namely; *Chlamydia trachomatis*.

Still another aspect of the invention is the provision of kits for DNA sequence detection, which kits comprise the polystyrene solid support and sets of PCR reagents including the specific primers and probes preselected for the amplification of the target DNA sequences that will hybridize with the capture probes. Such kits would also typically include the enzyme or enzymes needed for the PCR reaction, preferably a thermostable enzyme such as Tao (*Thermus aquaticus*) polymerase. In the case of the use of the microtiter plate, they would also include microtiter Plates with the capture probes for the specific target sequence already bound thereto.

DETAILED DESCRIPTION OF THE PREFERRED EMBODIMENTS

The terms "oligonucleotide", and "primer" used herein will have the meaning defined in the aforesaid U.S. Pat. No. 4,683,202. The term "capture probe" as used herein will be defined as an oligonucleotide which is completely or substantially complementary to the sequences of the amplicon within the boundaries of the primers. In the Present preferred embodiment, the capture probe is not tailed, but it may be tailed with deoxyribonucleotides or ribonucleotides.

In the practice of the present invention, the primers and probes are selected to be "substantially" complementary to the different strands of the target sequence to be amplified.

For one of the specific embodiments described herein, two sets of PCR primers and capture probes were selected from the nucleotide sequence of the cryptic plasmid of the *Chylamydia trachomatis* L1 serovar (Hatt et al., *Nucleic Acids Research*. 16: 4053-4067, 1988). This enabled the specific amplification and detection of C. trachomatis. For other general purposes, primer and probe selection for individual targets will be as described in the aforesaid U.S. Pat. No. 4,683,202.

As an alternative to, and improvement over known techniques for capturing the amplified sequence (amplicon) resulting from the application of PCR as previously described, the present invention, in its preferred embodiment, utilizes an oligonucleotide capture probe passively bound to the wells of the microtiter plate in order to capture (by sequence-specific hybridization) biotin-labelled amplicons. Avidin-horseradish Peroxidase is then employed to the biotinylated amplicons, and its reaction with the substrate (hydrogen peroxide) and chromogen (either OPD or TMB) yields a quantitative colorimetric signal. Again, as described in the aforesaid U.S. Pat. No. 4,683,202, deoxyribonucleotide triphosphates dATP, dCTP, dGTP and TTp are also added to the synthesis mixture in adequate amounts and the resulting solution is heated to about 90°-100° C. for about 0.5 to 10 minutes, to separate strands of template. After this heating period, the solution is quickly cooled to the temperature which is preferable for the primer template annealing. To this mixture is added an appropriate agent for inducing or catalyzing the Primer extension reaction, and the reaction is allowed to occur under conditions known in the art. The inducing agent may be any compound or system which will function to accomplish the synthesis of primer extension Products, including enzymes. Suitable enzymes for this purpose include, for example, *Eschericia coli* (*E. coli*) DNA polymerase I, Klenow fragment of *E. coli* DNA polymerase I, T4 DNA polymerase, other available DNA polymerases, reverse transcriptase, and other enzymes, including preferably heat-stable enzymes (viz. Tag DNA polymerase) which will facilitate incorporation of the nucleotides in the proper manner to form the primer extension products which are complementary to each nucleic acid strand.

The newly synthesized strand and its complementary nucleic acid strand form a double-stranded molecule, the strands of which are separated using any denaturation procedure to provide single-stranded molecules, preferably heat.

New nucleic acid is synthesized on the single-stranded template molecules. Additional enzyme, nucleotides and primers may be added if necessary for the reaction to proceed under the conditions Prescribed above. Again, the synthesis will be initiated at one end of the oligonucleotide Primers and will proceed along the single strands of the template to produce additional complementary nucleic acid by primer extension.

The steps of strand separation and extension product synthesis can be repeated as often as needed to produce the desired quantity of amplified nucleic acid sequence.

GENERAL LABEL TECHNIQUES

In general, any material (molecule, atom) may be used in the present invention to provide an indication or "signal" that is detectable (and preferably quantifiable) and which can be attached to or incorporated into the nucleic acid.

In a preferred embodiment of the present invention, two methods are employed to prepare amplicons which incorporate biotin labels during the PCR amplification. In the first case, biotin-11-dUTP (a TTP analog chemically modified with a biotin label) partially replaces TTP in the PCR reaction. The biotin-11-dUTP is incorporated by Tao DNA polymerase during primer extension, and the resulting DNA product is "internally" labelled with biotin.

In the second case, a chemical "linker arm" is attached to the 5' terminus of oligonucleotides bound to a solid support. In the preferred embodiment, the "linker arm" as used herein is a molecule which is chemically attached to the 5' primer terminus (by phosphoramadite chemistry) and is capable of covalently linking an amino group or groups to the oligonucleotide. The amino groups in turn are biotinylated with biotin-X-NHS These 5' biotin-labelled oligonucleotides, when used as primers in the PCR reaction, generate amplicons which are biotinylated at their 5' termini.

The "linker arm" can be any molecule which is long enough to act as a spacing agent to distance the label away from the oligonucleotide sequence, and also be amenable to the attachment of one or more suitable labels, thermostable enzymes or ligands.

In the preferred embodiment of the present invention, either or both of these two biotin-labelling procedures (incorporation of biotin-11-dUTP and 5' biotin-labelled primers) may be used to label the amplified products of PCR.

Besides biotin, other labels may also be used in this invention, including radiolabelled compounds, luminescent or fluorescent reagents, electron dense reagents, thermostable enzymes, ligands, antibody-hapten complexes, and chelating systems. The alternative labels must be compatible with the relatively harsh temperature conditions of PCR amplification, as well as conditions of denaturation and capture hybridization.

One such example of alternative labels includes digoxigenin-11-dUTP, which like biotin-11-dUTP, is incorporated by Tao polymerase into labelled, amplified DNA. Digoxigenin labelled amplicons can then be detected with an antibody against digoxigenin conjugated with alkaline phosphatase, followed by standard colorimetric detection as described herein.

Another example of an alternative label is $^{32}P$-labelled deoxynucleotide triphosphates, which also can be used to partially replace unlabelled deoxynucleotide triphosphates in the PCR reaction mix. The extent of capture hybridization could be determined, for instance, by scintillation counting of removable microtiter wells (described below, Step 2) after capture hybridization and washing.

POLYSTYRENE SOLID SUPPORT

The capture plate or support used in the present invention will be polystyrene solid support that has enhanced protein binding capacity. Various treatments of such support to accomplish such enhancement are known in the art (for example, irradiation with $^{60}Co$).

The polystyrene solid support can take any of several forms; e.g. microtiter plates, micromagnetic particles (available from Advanced Magnetics, Inc.); beads, strips, dipsticks, etc.

Preferably, the polystyrene support used in the present invention will be a microtiter plate having enhanced protein binding capacity and a plurality of wells, with the most preferable of such microtiter plates being those known as "Dynatech Immulon®2" (Dynatech Laboratories, Inc., Chantilly, Va, supplied by Fisher Scientific).

GENERAL HYBRIDIZATION TECHNIQUES

In a preferred embodiment of the present invention, an amplicon-specific oligonucleotide capture probe is passively bound to wells of an Immulon®2 polystyrene microtiter plate at a concentration of 25 ng DNA/ well, in a solution of 1 M ammonium acetate. Such microtiter plates have a multiplicity of wells and thus provide both high surface area and Permit a high number of simultaneous assays (e.g. 96).

In addition to the passive attachment of the capture Probe, alternative methods of attachment may be used, including but not limited to: covalent attachment; attachment via an intermediary protein (e.g., BSA); and attachment by any alternative chemical means.

The hybridization step of the present invention, more particularly the "capture hybridization" is preferably accomplished in the presence of 1 M guanidine thiocyanate, 20 mM ethylene diaminetetraacetic acid (EDTA) disodium salt, pH 8.0. The concentration range for accomplishing microtiter plate capture hybridization is preferably 0.5 to 2.0 Molar GuSCN and most preferably 1.0 to 2.0 M.

Other reagents may also be used to accomplish capture hybridization. For example, a solution of ammonium thiocyanate (0.5 to 5.0 M, most preferably 5.0 M) may be used in place of guanidine thiocyanate.

Another possible substitute for guanidine thiocyanate is a reagent consisting of: 30% (v/v) deionized formamide; 3×SSPE [1×SSPE=0.18 M NaCl; 10 mM NaPO4, pH 7.7; 1 mM EDTA]; 5% (w/v) dextran sulfate; 0.1% Triton X-100 (octyl phenoxy polyethoxyethanol; Sigma Chemical Co., St. Louis, Mo.).

The format for such hybridization includes the following steps:
1. Preparation of Capture Probe
2. Preparation of Microtiter Capture Plate
3. Dilution and Denaturation of Amplified, Labelled DNA
4. Capture Hybridization
5. Wash
6. Block
7. Addition of Avidin:Horseradish Peroxidase
8. Wash
9. Addition of Substrate and Chromogen; Color Development
10. Plate Reading (Quantification)

These steps will now be described in detail.
1. Preparation of Capture Probe

The capture probes herein are selected to be "substantially" complementary to sequences of the amplicon within the boundaries of the primers. Therefore, the capture probes must be sufficiently complementary to specifically hybridize to the amplicon under capture hybridization conditions. In the presently preferred embodiment, the capture probe typically contains 20-200 nucleotides.

Further, more than one capture probe may be used, and additional capture probes may be used to capture the same or opposite strand of the labelled amplicon.

Although the capture probe is defined herein as "sequences of the amplicon within the boundaries of the primers", the primers themselves, or oligonucleotides containing primer sequences, may also be used as capture probes. It should be noted, however, that when such oligonucleotides are used as capture probes, they must compete during hybridization with PCR primers which have not been removed from the reaction products.

The capture probes herein have been synthesized on a MilliGen 7500 DNA Synthesizer (MilliGen/Biosearch, Inc., Burlington, Mass.) by standard beta-cyanoethyl phosphoramadite chemistry, using procedures standard to those skilled in the art. Before use, the capture probes were partially purified by either electrophoresis through 15% (w/v) polyacrylamide gels or by spin column (See Example 3). The final partially purified capture probe was suspended in water, its concentration was determined spectrophotometrically, and it was stored at 4° C. until needed.

Although the capture probe as described herein is produced synthetically, it need not be. It may also be obtained as a subset of naturally occurring DNA prepared by standard means (e.g., restriction endonuclease digestion).

2. Preparation of Capture Plate

The oligonucleotide capture probe is preferably fixed to the wells of a Dynatech Immulon®2 polystyrene microtiter plate (Dynatech Laboratories, Inc., Chantilly, Va., supplied by Fisher Scientific). The Immulon®2 plate is an arrangement of 96 miniature polystyrene test tubes (wells) in a single plastic plate, designed for general use in microvolume solid phase immunoassay procedures. In the Preferred embodiment of the present invention, plates with flat bottom wells (400 μl volume capacity) are used, but it is assumed that "U" bottom wells may also be used (300 μl volume capacity).

As another preferred embodiment, the probe may also be fixed to Immulon®2 Removawell® strips (Dynatech), which are removable strips of twelve Immulon®2 polystyrene test tubes (wells) that are fitted into Removawell® strip holders (Dynatech) in a microtiter Plate format.

The oligonucleotide capture probe is diluted to yield 25 ng per microtiter well in 50 μl M ammonium acetate (Fisher Scientific, Fair Lawn, N.J.). "Blank wells" are also prepared by adding 1 M ammonium acetate (without oligonucleotide capture probe) to certain wells (to which labelled PCR products will be later added for mock hybridization). These blank wells are an indication of non-specific sticking of biotinylated DNA to wells of microtiter plates, and are used to calibrate the plate reading instrument (spectrophotometer) (See below, Step 10).

The plate is sealed with mylar plate sealer (Dynatech) and is incubated at 37° C. overnight for passive fixation of the oligonucleotide capture probe to the polystyrene surface. If the plates are not to be used immediately, they are stored at 4° C. until needed. Plates stored in this way for up to six weeks showed no significant difference in their ability to capture DNA.

Just prior to hybridization, the wells of the plates are washed twice with 200 μl of 2×SSC [1×SSC=0.15 M NaCl; 15 mM sodium citrate buffer, pH 7.0]and once with 200 μl of 2×SSC, 0.1% (v/v) Triton X-100. All plate washes described herein are done using a multiple channel pipet device (e.g., Titertek®), or may be done using an appropriate automatic microtiter plate washer.

3. Dilution and Denaturation of Amplified, Labelled DNA

The biotinylated PCR products are diluted (in a range of from 1:10 to 1:100 or more) in 1 M GuSCN (Ultra-pure grade; Boehringer Mannheim Biochemicals, Indianapolis, Ind.), 20 mM EDTA (Sigma), pH 8.0 (prepared from a 5×stock), heated at 100° C. for five minutes and quickly chilled in an ice water bath. [The heating step accomplishes heat denaturation of the PCR products, and the quick cooling discourages reannealing of amplicon strands, favoring hybridization to the oligonucleotide capture probe.]Aliquots of 100 μl are loaded to each well, including the wells designated as "blanks" (no capture probe) as described above (Step 2).

4. Capture Hybridization

Specific capture of amplified, labelled DNA by oligonucleotide capture probe is accomplished by incubation at room temperature for 1-3 hours. During this time, PCR amplicons are specifically captured by the oligonucleotide capture probe, based on sequence complementarity between the capture probe and labelled amplicon.

5. Plate Wash

Following hybridization, the contents of all microtiter wells are discarded and the wells are washed two times with 200 μl of 2×SSC, 0.1% (v/v) Triton X-100; and four times with 200 μl of 0.2×SSC, 0.1% (v/v) Triton X-100, previously warmed to 37° C. These washes are performed to remove unbound biotinylated products from the microtiter wells.

6. Block

Following plate washing, the wells of the plate are then "blocked" for a minimum of 15-30 minutes with 200 μl of a solution of PBS, (PBS=0.13 M NaCl, 7 mM $Na_2HPO_4$, 3 mM $NaH_2PO_4$, pH 7.0), 2% (w/v) bovine serum albumin (BSA) (Sigma), 0.1% (v/v) Triton X-100. This "blocking" step is required to minimize non-specific binding of avidin:HRP to microtiter wells.

7. Avidin:Horseradish Peroxidase

Avidin:horseradish peroxidase (HRP) complex (Vector Laboratories, Inc., Burlingame, Calif.) is diluted 1:2000 in PBS, 0.1% (v/v) Triton X-100, to a final concentration of 2.5 μg avidin:HRP/ml. Fifty microliters of diluted avidin:HRP are added to each well, and incubated for 30 minutes at room temperature. During this step, the avidin:HRP complex binds tightly to captured biotinylated Products on the well. While avidin:HRP is used in the present invention, a complex of streptavidin:HRP may be used instead. Likewise, other compounds complexed with avidin (or streptavidin) may be used, including: alkaline phosphatase, beta-galactosidase, luciferase, fluorescein, Texas Red or any other agent capable of generating a colorimetric, fluorescent or luminescent signal.

8. Wash

The wells of the microtiter plate are then washed four times with 200 μl PBS, 0.1% Triton X-100; and once with 200 μl PBS, 1 mM EDTA, the final wash incubated at room temperature for 1-10 minutes. These washes are performed to remove unbound avidin:HRP from microtiter wells prior to adding chromogen.

9. Color Development

Color development, in the preferred embodiment of the present invention, is accomplished using either of two chromogen systems: (a) hydrogen peroxide/OPD and (b) hydrogen peroxide/TMB.

(a) Hydrogen peroxide/OPD. After the wash buffer (described in Step 8) has been removed, 150 μl OPD reagent [1.6 mg/ml o-phenylene diamine disodium salt (Sigma), 0.0125% (v/v) hydrogen peroxide (Fisher Scientific) in 0.15 M sodium phosphate/citrate buffer, pH 6.0] is added and color development is allowed to proceed in the dark for 1-30 minutes. Color development is stopped by the addition of 50 μl 4 N $H_2SO_4$.

(b) Hydrogen peroxide/TMB. After the final wash buffer (described in Step 8) has been removed, 100 μl TMB color reagent is added to each well. [TMB color reagent consists of freshly mixing equal volumes of TMB peroxidase substrate (3,3',5,5'-tetramethylbenzidine at a concentration of 0.4 g/l in an organic base; commercially available from Kirkegaard and Perry, Inc., Gaithersburg, Md.) and hydrogen peroxide solution [0.02% (v/v) hydrogen peroxide in citric acid buffer; commercially available from Kirkegaard and Perry, Inc.]. The reaction is allowed to proceed at room temperature in the dark for 1-30 minutes, at which time color development is stopped by the addition of 100 μl M phosphoric acid ($H_3PO_4$).

The TMB substrate produces a precipitate with a blue color. Upon addition of phosphoric acid, a color change to yellow occurs, with an optical density measured at 450 nm (see below, Step 10). In addition to HRP substrates OPD and TMB, other soluble substrates include: 2,2-azino-di (3-ethylbenzthiazoline sulfonic acid)(ABTS) and 5-aminosalicylic acid (ASA). Insoluble substrates include 3-amino-9-ethylcarbazole (AEC) and 3,3-diaminobenzidene (DAB).

10. Plate Reading (Quantification)

After color development is stopped, the optical density (OD) of samples in each well is determined by reading in an automatic microtiter plate reader capable of spectrophotometric determination (e.g. InterMed Immunoreader® NJ-2000) at wavelengths specific for the chromogen used (see below).

The OD of blank wells [biotinylated PCR products added to well without capture probe, as described in Step 2] is also determined. This signal (usually very low) is an indication of spurious "non-specific" sticking of biotinylated products to sample wells, rather than signal resulting from bona fide capture of biotinylated amplicons through hybridization with a capture probe. Thus, the OD of blank wells is subtracted from the OD of sample wells to give an accurate quantification of bona fide capture hybridization.

The appropriate wavelength setting for the spectrophotometer (plate reader) is dependent on the specific chromogen used for the colorimetric reaction. Thus, if using hydrogen peroxide/OPD, the correct wavelength setting is 490 nm; if using hydrogen peroxide/TMB, the correct wavelength setting is 450 nm.

Through the use of the present invention, various infectious diseases can be diagnosed by detecting the presence of the specific DNA sequences that characterize the causative microorganism; such as bacteria (e.g. *Chlamydia, Salmonella,* etc); viruses (e.g. hepatitis virus); various parasites (e.g. malaria-inducing); etc. Specifically, the invention will be useful in detecting Human Immunodeficiency Viruses 1 and 2 (HIV 1 and HIV 2), Human T Lymphotropic Viruses I and II (HTLV-I and HTLV-II), Hepatitis B Virus (HBV), Hepatitis C Virus (HCV), Human Papilloma Virus (HPV) and *Pneumocyctis carinii.* As previously described, and as an additional embodiment of the invention, novel capture Probes and Primers have been discovered that are specifically capable of use in the detection of the organism *Chlamydia trachomatis.* Such novel probes and primers will be described in detail in the following specific examples.

The present invention also offers particular advantages in the context of clinical application. Through the use of the microtiter plates, a convenient, rapid, simple, economic and automatable assay Procedure is provided. The assay is highly accurate and sensitive as compared to conventional means and can be conducted at a fraction of the time normally needed.

The following examples are now offered by way of illustration and are not intended to be limiting.

EXAMPLE 1

Synthesis of Biotin-11-dUTP

Biotin-11-dUTP was chemically synthesized by the methods of Ward et al., *Proc. Natl. Acad. Sci. (USA),* 78:6633-6637 (1981), and was suspended at a concentration of 0.4 mM in 100 mM Tris-HCl, pH 7.5, 0.4 mM EDTA. The ratio of biotin-11-dUTP:TTP was optimized, and the highest signal was obtained using a ratio of 4:1 (biotin-11-dUTP:TTP).

EXAMPLE 2

Preparation of 5' Biotinylated Primers

All oligonucleotides used as PCR primers were synthesized on a MilliGen 7500 automated DNA synthesizer by standard beta-cyanoethyl phosphoramadite chemistry, using Procedures standard to those skilled in the art.

Figure 1:
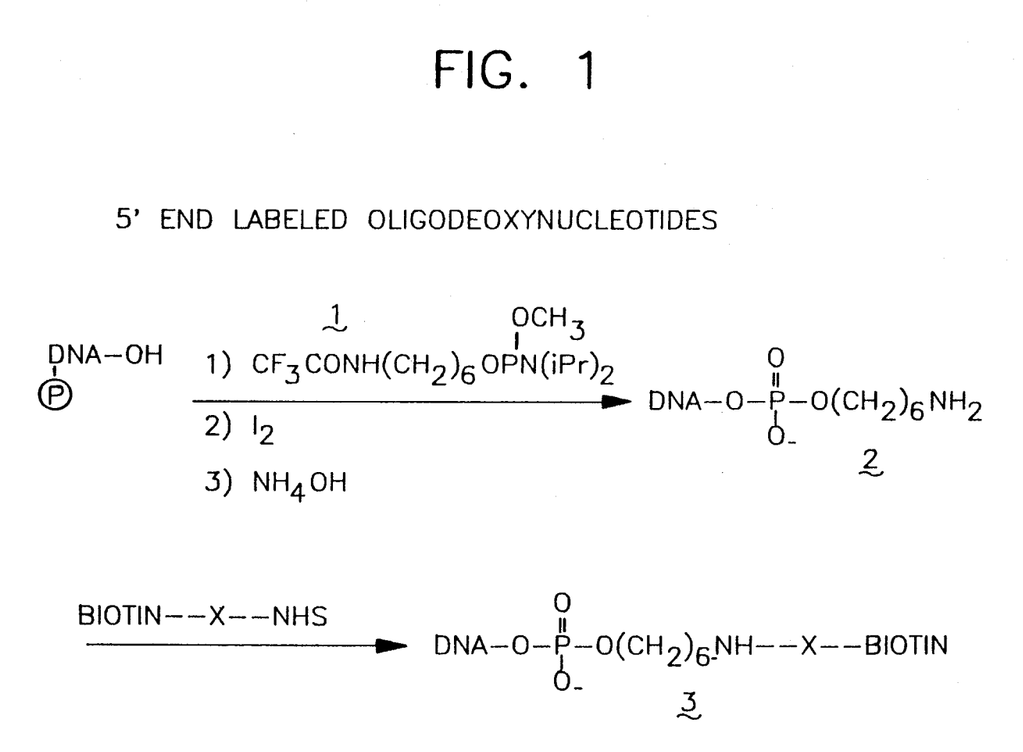
FIG. 1 illustrates the preparation of a chemical linker arm which was modified to enable biotinylation of oligonucleotide PCR primers.

Oligonucleotides prepared for use as biotinylated Primers were modified as shown in FIG. 1. The synthetic oligonucleotides on solid support were derivitized at the 5' end by reaction with the protected hexylamino Phosphoramadite [structure 1], followed by oxidation and deprotection according to standard procedures (McBride and Caruthers, *Tetrahedron Letters,* 24:245-248, 1983) to afford 5' amino labelled oligomers [structure 2]. The reaction of [2] with N-hydroxysuccinimidyl esters of biotin derivatives gave 5' biotinylated oligonucleotides [structure 3] in good yields, which were purified by polyacrylamide gel electrophoresis. (See below, Example 3.)

EXAMPLE 3

Purification of Oliconucleotides

Oligonucleotides used as PCR primers or capture probes were purified in one of two ways: (a) polyacrylamide gel electrophoresis or (b) spin column.

(a) Polyacrylamide Gel Electrophoresis Aliquots of 100-250 μg each oligonucleotide were dried in vacuo, resuspended in a minimal volume of gel loading buffer [TBE (89 mM Trisborate, 89 mM boric acid, 2 mM EDTA); 90% (v/v) deionized formamide; 0.02% (w/v)

bromophenol blue], heated at 100° C. for 5 minutes, and quickly cooled in an ice water bath. Samples were loaded onto a denaturing polyacrylamide gel [15% (w/v) acrylamide (acrylamide:bis-acrylamide, 29:1) (IBI, New Haven, Conn.), 7 M urea (IBI) in TBE]and electrophoresed at 650 volts for four hours. The DNA was visualized by uv shadowing over a thin layer chromatography plate (Eastman Kodak #13254 cellulose), photographed, and the gel band of full-length oligonucleotide was excised. The gel piece was crushed and DNA was eluted in water overnight at 37° C. The DNA was further purified by passage over a $C_{18}$ Sep cartridge (Waters Associates, Milford, Mass.), and eluted in 40% (v/v) acetonitrile (Fisher). After evaporation to dryness in vacuo, the DNA was suspended in water and its concentration was determined spectrophotometrically. Stock concentrations were adjusted with water and stored at 4° C. until needed. (b) Soin Column Some oligonucleotide capture probes and primers were partially purified using Bio-SpinTM 6 columns (Bio-Rad, Inc., Richmond, Calif.) in a swinging bucket rotor at low centrifugal forces, following manufacturer's instructions for the spin column. After partial purification, the concentration of oligonucleotides was determined spectrophotometrically, and stock solutions were prepared with water and stored at 4° C. until needed.

EXAMPLE 4

PCR Conditions

Most primer pairs were tested empirically to determine their optimal temperature conditions for PCR amplification, with particular attention paid to the annealing temperature.

For detection of HTLV-1 tax sequences, primer set SK43 and SK44 (described by Kwok et al., *J. Inf. Dis.*, 158 1193–1197, 1988) was used. Using this primer pair, a 100 µl PCR reaction consisted of: 1×reaction buffer (RB) [10×RB=500 mM KCl; 100 mM Tris-HCl, pH 8.5; 25 mM $MgCl_2$]; 200 µM each of dATP, dCTP, dGTP and TTP; 50 pmole each of SK43 and SK44 and 2 units recombinant Tao DNA Polymerase (RecombiTaq®, Cetus Perkin Elmer, Norwalk, Conn.).

For experiments in which biotin-11-dUTP was incorporated, the reaction contents were as above, except that 200 µM TTP was replaced with 160 µM biotin-11-dUTP, 40 µM TTP.

For primer set SK43 and SK 44, the PCR temperature regime began with an initial extended denaturation at 94° C. for 5 minutes, followed by an annealing step at 50° C. for 25 seconds, and an elongation step at 72° C. for 1 minute. For the next 28 cycles, the temperature regime consisted of: denaturation at 94° C. for 25 seconds, annealing at 50° C. for 25 seconds and extension at 72° C. for 1 minute. The final (thirtieth) cycle was: denaturation at 94° C. for 25 seconds, annealing at 50° C. for 25 seconds and an extended elongation at 72° C. for ten minutes. After PCR amplification, 90 µl of reaction contents were removed from under the mineral oil and stored at 4° C. until analysis of PCR products.

Example 5

Preparation of Positive and Negative Control Plasmid Templates

A plasmid (pTAX) containing the entire tax gene of HTLV-1 was used as a positive control template. The concentration of plasmid DNA was determined spectrophotometrically, and dilutions were made in water to deliver known copy numbers of target DNA to PCR reactions. In this way, a positive control template was devised.

A heterologous plasmid was also used with the HTLV-1 tax primer set, as a PCR negative control. This plasmid, pRT-POL, contained sequences of the HTLV-1 polymerase (ool) region. The plasmid DNA concentration was determined, and was diluted serially as described above for pTAX. The plasmid concentrations were calculated to deliver a known copy number in a specific volume added to the PCR reaction mix (i.e., 2 µl template DNA added to 98 µl reaction mix).

EXAMPLE 6

Amplification of HTLV-1 tax Target, Unlabelled Amplicons

In order to directly compare three PCR detection systems side-by-side, known copy numbers of plasmid pTAX (Example 5) were amplified by PCR. The plasmid concentration was adjusted with water to deliver 1300, 100, 50, 20 or 10 copies of template per reaction. HTLV-1 tax primer set SK44 (Kwok et al., *J. Inf. Dis.*, 158:1193–1197, 1988) was synthesized and Purified by Bio-SPin® 6 spin columns (described in Example 3), and each primer was added to the PCR reaction at a concentration of 50 pmoles.

Unlabelled amplified DNA was generated by using each of the four dNTPs at 200 µM for PCR amplification. These unlabelled PCR products were used for determining detection sensitivity of Southern blot hybridization (Example 9) and oligonucleotide hybridization (OH) (Example 10) assays. Amplification proceeded for 30 cycles using the reaction mix and temperature conditions as described in Example 4.

EXAMPLE 7

Amplification of HTLV-1 tax, Biotin-11-dUTP Incorporation

PCR amplification with primer set SK43/SK44 was also done to produce biotinylated amplicons, through the incorporation of biotin-11-dUTP. Conditions for this HTLV-1 tax amplification were as described above (Example 6), except that the reaction mix included dATP, dCTP and dGTP at 200 µM; biotin-11-dUTP at 160 µM; TTP at 40 µM. The biotin-labelled PCR products were used to determine detection sensitivity of plate capture hybridization (Example 8) and Southern blot hybridization (Example 9). Amplification proceeded for 30 cycles using the reaction mix and temperature conditions as described in Example 4.

EXAMPLE 8

Plate Capture Assay

A capture plate was prepared by binding 25 ng oligonucleotide "capture probe" SK45 (Kwok et al., *J. Inf. Dis.*. 158:1193–1197, 1988) in 1 M ammonium acetate to wells of a Dynatech Immulon® 2 plate, and incubating overnight at 37° C. The biotinylated products of PCR (Example 7) were diluted 1:25 and 1:100 in 1 M guanidine thiocyanate (GuSCN), heat denatured (five minutes, 100° C.) and quick cooled in an ice water bath. For each sample and control, 100 ul were added to each of four microtiter wells (triplicate SK45 capture probe wells and one "blank" well), and incubated for hybridization two hours at room temperature. The contents of the plates were discarded, and the plates were washed, blocked, and treated with avidin:horseradish peroxidase, as described above in Step 9. After adding $H_2O_2$ and OPD, color development was determined at 490 nm using a plate reader.

The results of the plate capture hybridization are included below. Referring to the table below, capture by hybridization of biotinylated PRR products is illustrated using HTLV-1 primers SK43/SK44 specific for HTLV-1 tax. amplifying homologous template (pTAX) and heterologous template (pRT-POL). Biotin-11-dUTP was added as a precursor into the PCR reaction (See Example 7), and PCR conditions were as described for Example 4. Plate capture assay was done as described. Samples were diluted 1:25 and 1:100 in 1 M GuSCN for hybridization, after which plates were washed, blocked, and treated with avidin-HRP. $OD_{490}$ was determined after 35 minutes color development with $H_2O_2$/OPD. Numbers presented below are averages of sample triplicates.

|  | $OD_{490}$ 1:25 Dilution | $OD_{490}$ 1:100 Dilution |
| --- | --- | --- |
| 1300 copies pTAX | 1.693 | 0.444 |
| 100 copies PTAX | 0.343 | 0.117 |
| 50 copies pTAX | 0.300 | 0.053 |
| 20 copies pTAX | 0.123 | 0.040 |
| 10 copies pTAX | 0.031 | 0.029 |
| NEGATIVE CONTROLS: |  |  |
| No Template | 0.007 | 0.026 |
| $10^4$ copies pRT-POL | 0.000 | 0.042 |

The detection limit for this assay appeared to be 20 copies of clean target plasmid ($OD_{490}$ of 1:25 dilution was 0.123). The "no template" negative control and the negative control using a heterologous amplification template gave OD values of <0.020.

EXAMPLE 9

Agarose Gel Electrophoresis and Southern Blot Hybridization

Aliquots (25 ul) of both unlabelled (Example 6) and biotin-labelled (Example 7) PCR products were dried in vacuo resuspended in 5 $\mu l$ water and 2 $\mu l$ agarose gel loading buffer [0.25% (w/v) bromophenol blue, 0.25% (w/v) xylene cyanol, 30% (v/v) glycerol] and loaded on a 3% (w/v) NuSieve® GTG (FMC BioProducts, Rockland, Me.)/ 1% (w/v) Sea Kem (FMC) agarose gel in TBE, containing 0.5 $\mu g/ml$ ethidium bromide. The gel was visualized with a uv transilluminator and photographed. The gel was then treated for 30 minutes in 0.5 N NaOH, 1 M NaCl and for 30 minutes in 0.5 M Tris-HCl, pH 7.5, and blotted overnight to Nytran® (Schleicher and Schuell, Inc., Keene, HN) nylon membranes in high salt, following standard procedures known in the art. The blot ("Southern blot") was then baked 30 minutes at 75° C. and prehybridized 1–4 hours at 37° C. in a sealed bag containing 6×SSPE [1×SSPE=0.18 M NaCl, 10 mM NaPO4, pH 7.7, 1 mM EDTA]; 1% (w/v) sodium docecyl sulfate (SDS) (Aldrich Chemical Co., Milwaukee, Wis.); 10×Denhardt's reagent [1% (w/v) each of ficoll (Pharmacia, Piscataway, N.J.), polyvinylpyrrolidone (Sigma), and BSA (Sigma)]; and 50 $\mu g/ml$ salmon sperm DNA, heat denatured and quick cooled.

Figure 2:
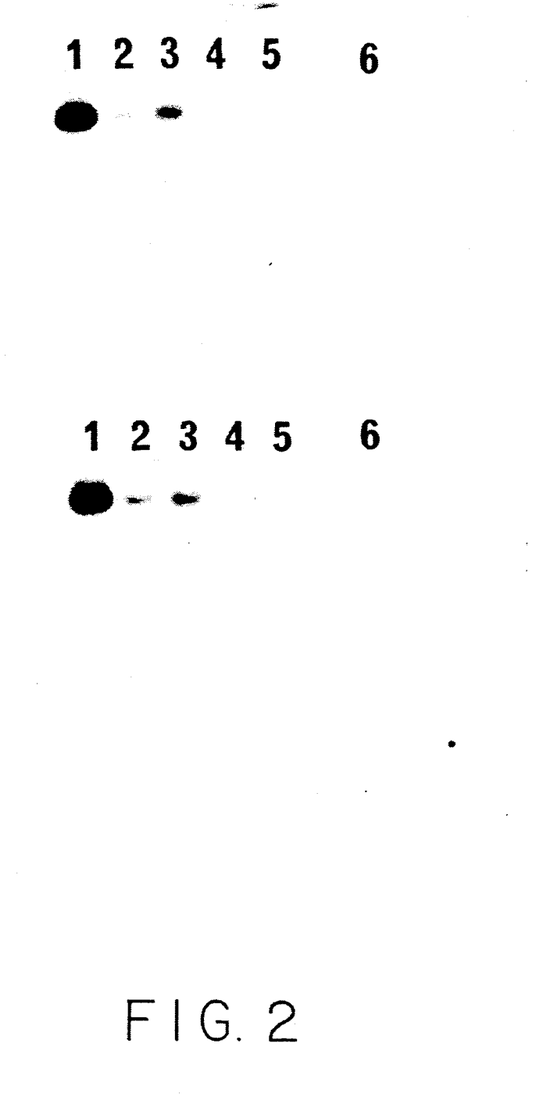
FIG. 2 illustrates the results of an autoradiogram of PCR products bound to Nytran® membrane.

In FIG. 2, PCR amplification was as described in Examples 6 and 7, and conditions for agarose gel electrophoresis, blotting, prehybridization and hybridization were as described in this Example.

In the upper half of the photograph, Biotin-labelled PCR products of Example 7 are shown: amplified products of 1300, 100, 50, 20 and 10 copies of pTAX (Lanes 1–5, respectively); PCR "no template" negative control (Lane 6).

In the lower half of the photograph are shown the unlabelled PCR products of Example 6: amplified products of 1300, 100, 50, 20 and 10 copies of PTAX (Lanes 1–5, respectively); PCR "no template" negative control (Lane 6).

An amplicon-specific probe, SK45, was labelled with $^{32}$P-ATP using polynucleotide kinase (Boehringer Mannheim Biochemicals), using procedures standard in the art. For hybridization, this radiolabelled probe was added to hybridization buffer (6×SSPE, 1% (w/v) SDS) at a rate of $4.1 \times 10^6$ cpm/blot. After hybridization at 60° C. for 2–3 hours, the blot underwent several stringency washes and was placed under Kodak X-OMAT AR film overnight at $-80°$ C. with an intensifying screen.

After overnight exposure, the detection limit for the Southern blot was 10 copies of plasmid pTAX target for PCR Products that were not biotinylated (Example 6), and 20 copies of plasmid target for biotinylated PCR products (Example 7). (See photograph of autoradiogram, FIG. 2.) The "no template" PCR negative control gave no detectable product on autoradiography.

EXAMPLE 10

Oligonucleotide Hybridization Assay

Figure 3:
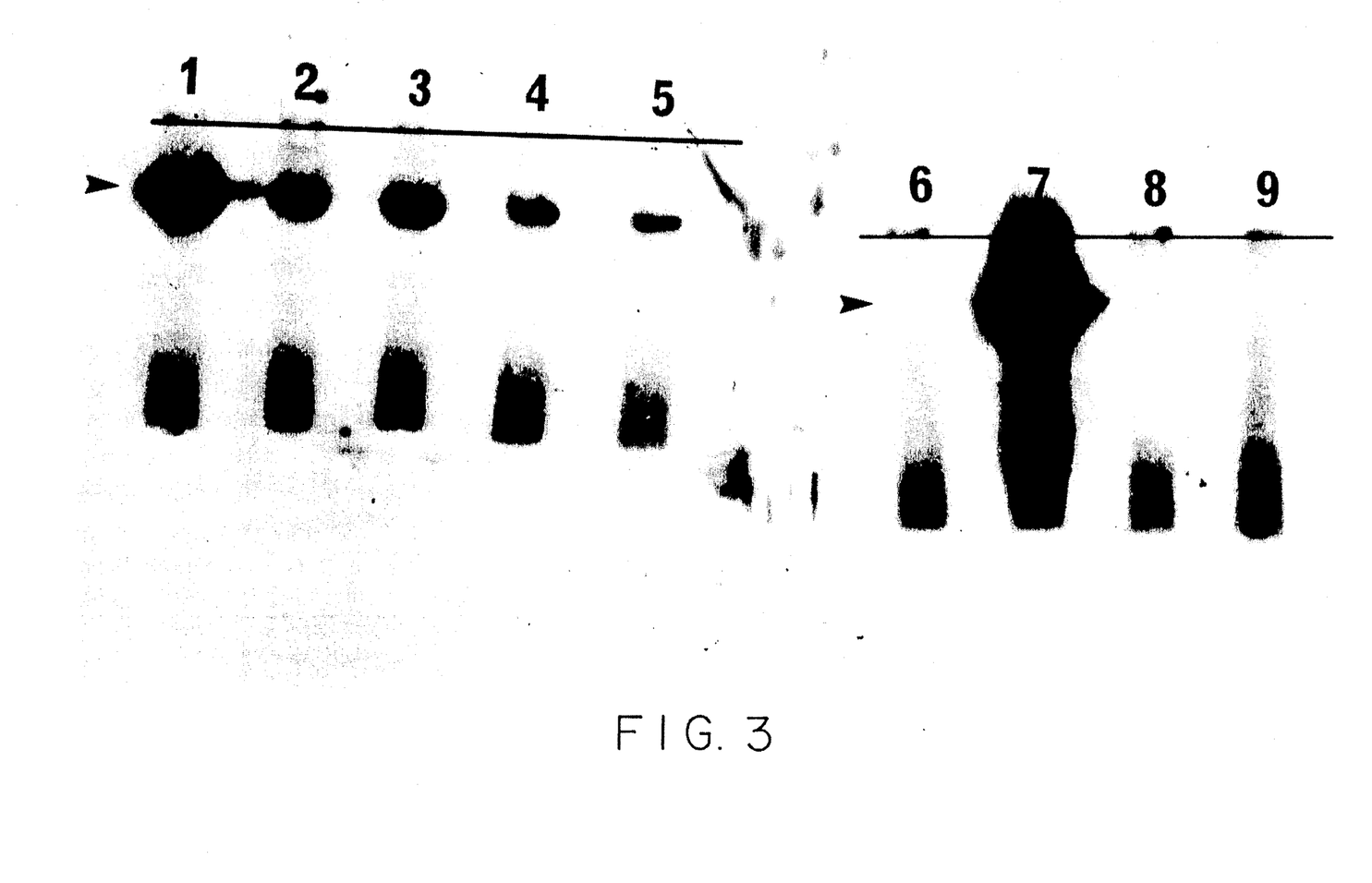
FIG. 3 illustrates the results of oligonucleotide hybridization (OH) assay using PCR products of Example 6.

Referring to FIG. 3, the conditions of OH assay (preparation of labelled probe, denaturation and annealing conditions and conditions for polyacrylamide gel electrophoresis) were as described in this Example.

The photograph shown is an overnight exposure ($-80°$ C., with intensifying screen on Kodak X-OMAT AR film) of autoradiogram, showing signal generated from either 1300, 100, 50, 20 or 10 copies of pTAX (Lanes 1–5, respectively); "no template" PCR negative control (Lane 6); $10^4$ extracted Jurkat cells constitutively expressing HTLV-1 tax. amplified by PCR (Lane 7); $10^4$ extracted Jurkat cells, amplified by PCR (Lane 8); OH negative control in which no amplified DNA was added to $^{32}$P-SK45 for OH assay (Lane 9)

The unlabelled PCR products from primer set SK43/SK44 (Example 6) were analyzed by oligonucleotide hybridization assay (OH assay) to determine the limit of detection for this format. The procedure was essentially as described by Abbott et al., J. Inf. Dis. 158-1158-1169 (1988) for liquid hybridization (LH). Thirty microliters of PCR amplified product were added to 10 $\mu l$ of a probe mixture containing 250,000–400,000 cpm of $^{32}$P labelled SK45 probe diluted in 44 mM EDTA, 66 mM NaCl. The DNA mixture was denatured at 95° C. for five minutes, followed immediately by annealing to probe at 55° C. for 15 minutes. Ten microliters of agarose gel loading buffer (Example 9) were added, and half volume was loaded to a native 10% (w/v) polyacrylamide gel (acrylamide:bisacrylamide, 19:1) in TBE. Electrophoresis was at 200 volts until the bromophenol blue reached the bottom gel front. The upper half of the gel was exposed to Kodak X-Omat AR film for exposures of 3 hours and overnight, at $-80°$ C. with an intensifying screen.

After either a three hour or overnight exposure, ten copies of amplified plasmid pTAX target can clearly be seen as a specific band (FIG. 3). The "no template"

negative control and other negative controls produced no bands.

EXAMPLE 11

Assay Comparison and Discussion of Results

The plate capture assay (Example 8) was compared to more conventional assays, Southern blot hybridization (Example 9) and oligonucleotide hybridization (OH) assay (Example 10), for the ability to detect minimal copy numbers of target HTLV-1 DNA after 30 cycles of PCR amplification (Examples 6 and 7). Each of the three detection systems tested (plate capture assay, Southern blot and OH assay) were essentially comparable in their ability to detect small copy numbers of clean target plasmid after thirty cycles of PCR amplification. The plate capture was found to detect 20 copies, the Southern blot between 10 and 20 copies, and OH, 10 copies of clean target. Of the three detection systems, the plate assay is fastest, giving a definitive result in hours Moreover, the plate assay provides numerical OD values, as opposed to subjective autoradiogram bands with Southern blot and OH assays. Therefore, the present invention enables the objective numerical determination of "positivity" of a sample, and the calculation of an objective cut-off value for the lower limits of positivity. (This cut-off value is an OD value, below which samples are considered to be negative with a calculated degree of statistical significance.)

The OD values provided by the plate assay also allow for the quantitative determination of a "signal to noise" ratio, which is of importance in the validation of a diagnostic test. For the Southern blot hybridization and OH assay formats, "signal to noise" can be only estimated by a visual evaluation of signal from autoradiography.

EXAMPLE 12

Detection of Chlamydia trachomatis sequences

Two sets of primers and capture probes were synthesized to specifically detect *Chlamydia trachomatis*. The oligonucleotide sequences were chosen from the cryptic plasmid of the *C. trachomatis* L1 serovar (Hatt et al., *Nucleic Acids Research*, 16:4053–4067, 1988).

Primer set A generated a 208 bp specific amplicon, using the following primers:
CP-24 (25-mer, +polarity, bases 195–219)

5' GGG ATT CCT GTA ACA ACA AGT CAG G 3' i.e, the primer is any oligonucleotide which will bind to or cause elongation through the following sequence:

5' CC CTG ACT TGT TGT TAC AGG AAT CCC 3'

CP-27 (26-mer, - polarity, bases 377–402)

5' CCT CTT CCC CAG AAC AAT AAG AAC AC 3' i.e, the primer is any oligonucleotide which will bind to or cause elongation through the following sequence:

5' GT GTT CTT ATT GTT CTG GGG AAG AGG 3'

The primer set A 208 bp specific amplicon was detected with capture probe CP-35:

CP-35 (26-mer, - polarity, bases 235–260)

5' CAT AGC ACT ATA GAA CTC TGC AAG CC 3' i.e, the probe is any oligonucleotide which will bind to the following sequence:

5' GG CTT GCA GAG TTC TAT AGT GCT ATG 3'

Chlamydia primer set B generated a 173 bp specific amplicon using the following primers:
CP-37 (23-mer, +polarity, bases 678–700)

5' GTC CTG CTT GAG AGA ACG TGC GG 3' i.e, the primer is any oligonucleotide which will bind to or cause elongation through the following sequence:

5' CC GCA CGT TCT CTC AAG CAG GAC 3'

CP-38 (24-mer, - polarity, bases 827–850)

5' CTC CCA GCT TAA GAA CCG TCA GAC 3' i.e, the primer is any oligonucleotide which will bind to or cause elongation through the following sequence:

5' GTC TGA CGG TTC TTA AGC TGG GAG 3'

The primer set B 173 bp amplicon was detected with capture probe CP-39:
CP-39 (23-mer, - polarity, 726–748)

5' TGT CTT CGT AAC TCG CTC CGG AA 3' i.e, the probe is any oligonucleotide which will bind to following sequence:

5' TT CCG GAG CGA GTT ACG AAG ACA 3'

Primer set B was used to amplify target plasmid pCHL-1 Using 5' biotinylated primers, the target was amplified with 30 cycles of PCR, and the biotinylated products were examined by capture hybridization (See below). After ten minutes color development (TMB/H$_2$O$_2$), as few as 20 starting copies of pCHL-1 were detectable (1:25 dilution, OD$_{450}$=0.140), with negligible background signal (OD$_{450}$=0.009 for 1:25 dilution).

|  | OD$_{450}$ 1:25 | OD$_{450}$ 1:100 |
| --- | --- | --- |
| 10$^4$ copies pCHL-1 | >1.500 | >1.500 |
| 10$^3$ copies pCHL-1 | >1.500 | 1.286 |
| 10$^2$ copies pCHL-1 | 0.686 | 0.170 |
| 50 copies pCHL-1 | 0.215 | 0.050 |
| 20 copies pCHL-1 | 0.140 | 0.035 |
| Negative Control | | |
| No template | 0.009 | 0.000 |

EXAMPLE 13

Detection of McCoy Cells and Clinical Isolates Infected With Chlamydia Trachomatis McCoy cells, either uninoculated or infected with *C. trachomatis*, were lysed in 2SP (20 mM sodium phosphate buffer, pH 7.2, 2 M sucrose) containing 100 μg/ml Proteinase K, 1% Tween-20 and were incubated at 55° C. for 1 hour, followed by incubation at 95° C. for ten minutes. Primer Set A (Example 12) was used in a 30 cycle PCR amplification, and the products were examined by plate assay as described in Example 4. After ten minutes color development, both 10 and 100 infected McCoy cells, when spiked in $10^5$ uninfected McCoy cells, gave $OD_{450}$ values >2.000 (for both 1/25 and 1/100 dilutions of product in GuSCN). Extracted and amplified uninfected cells alone ($10^5$ cells) gave $OD_{450}$ values of <0.050.

Clinical specimens, previously graded for extent of cytopathic effects (CPE) [in a range of "negative" (no CPE) to 4+(most prominent CPE)], were likewise extracted and amplified for 30 cycles of PCR, using Primer Set A. The results of this assay are included below:

| | | $OD_{450}$ | |
|---|---|---|---|
| Culture Rating | Volume of Lysed Specimen | 1/25 Dilution in GuSCN | 1/100 Dilution in GuSCN |
| 4+ | 90 ul | >2.000 | 1.686 |
| 1+ | 90 ul | 0.145 | 0.086 |
| Negative | 90 ul | <0.050 | <0.050 |
| 4+ | 10 ul | >2.000 | 1.417 |
| 1+ | 10 ul | <0.050 | <0.050 |
| Negative | 10 ul | <0.050 | <0.050 |

In summary, novel ways of labelling and detecting the amplified products of PCR are herein described. These labelling and capturing procedures offer several advantages over conventional methods of detection:

1. The biotinylation and capture of PCR products on microtiter plates is a faster assay. The plate assay in the present invention can be accomplished in 2 hours, compared to about 6-24 hours for OH assay, and as much as 48 hours for Southern blotting and hybridization.
2. The plate assay format is less labor intensive, and may be amenable to automation for analysis of large numbers of samples.
3. Unlike the other two assay formats examined, the plate assay format does not require the preparation, Purification or handling of dangerous radioactive probes of high specific activity.
4. The capture of biotinylated products via plate assay provides an objective, quantitative evaluation of hybridization; the calculation of a statistical cut-off point for positivity of samples; and the quantitative calculation of an assay "signal-to-noise" ratio.

Many modifications and variations of this invention may be made without departing from its spirit and scope, as will become apparent to those skilled in the art. The specific embodiments described herein are offered by way of example only, and the invention is to be limited only by the terms of the appended claims.

We claim:

1. A diagnostic kit for the detection of a target nucleic acid sequence of *Chlamydia trachomatis*, said kit comprising PCR primers wherein said primers are oligonucleotides that will bind to or cause elongation through the following sequences:

5' CCTGACTTGTTGTTACAGGAATCCC 3'
   and 5'
   GTGTTCTTATTGTTCTGGGGAAGAGG 3' and a microtiter plate having a plurality of wells and having bound thereto oligonucleotide capture probe having a nucleic acid sequence substantially complementary to said target sequence.

2. The diagnostic kit of claim 1 which additionally comprises reagents for conducting the PCR amplification and hybridization of said capture probe and said target sequence.

3. The diagnostic kit of claim 2 which additionally comprises Tao polymerase and dNTP's.

4. The diagnostic kit of claim 3 wherein one or more of said dNTP's comprise a labelling agent.

5. The diagnostic kit of claim 1 wherein at least one of said PCR primers is biotinylated through a linker arm modification at the 5' terminus.

6. The diagnostic kit of claim 1 wherein said microtiter plate comprises polystyrene having enhanced protein binding capacity.

7. The diagnostic kit of claim 1 wherein said probe is a oligonucleotide that will bind to the following sequence:

5' GGCTTGCAGAGTTCTATAGTGCTATG 3'.

8. The diagnostic kit of claim 1 which is suitable for detection of *Chlamydia trachomatis* and wherein said primers are oligonucleotides that will bind to or cause elongation through the following sequences:

5' CCGCACGTTCTCTCAAGCAGGAC 3' and 5'
   GTCTGACGGTTCTTAAGCTGGGAG 3'.

9. The diagnostic kit of claim 8 wherein said probe is a oligonucleotide that will bind to the following sequence:

5' TTCCGGAGCGAGTTACGAAGACA 3'.

10. Primers for use in the PCR amplification of *Chlamydia trachomatis* nucleic acid target sequence, said primers being oligonucleotides that will bind to or cause elongation through the following sequences:

5' CCTGACTTGTTGTTACAGGAATCCC 3'
    and 5'
    GTGTTCTTATTGTTCTGGGGAAGAGG 3'.

11. Probes useful in hybridization assays of DNA sequences amplified with the primers of claim 10, said probes being oligonucleotides that will bind to the following sequence:

5' GGCTTGCAGAGTTCTATAGTGCTATG 3'.

12. Primers for use in the PCR amplification of *Chlamydia trachomatis* nucleic acid target sequence, said primers being oligonucleotides that will bind to or cause elongation through the following sequences:

5' CCGCACGTTCTCTCAAGCAGGAC 3' and 5'
    GTCTGACGGTTCTTAAGCTGGGAG 3'.

13. Probes useful in hybridization assays of DNA sequences amplified with the primers of claim 12, said probe being an oligonucleotide that will bind to the following sequence:

5' TTCCGGAGCGAGTTACGAAGACA 3'.

14. A method of detecting *Chlamydia trachomatis* by PCR amplification and hybridization assay comprising utilizing in said PCR amplification primers which are oligonucleotides that will bind to or cause elongation through the following sequences:

5' CCTGACTTGTTGTTACAGGAATCCC 3'
    and 5'
    GTGTTCTTATTGTTCTGGGGAAGAGG 3'.

15. The method of claim 44 wherein said hybridization assay further utilizes a capture probe and wherein said capture probe is an oligonucleotide that will bind to the following sequence:

5' GGCTTGCAGAGTTCTATAGTGCTATG 3'.

16. A method of detecting *Chlamydia trachomatic* by PCR amplification and hybridization assay comprising utilizing in said PCR amplification primers which are oligonucleotides that will bind to or cause elongation through the following sequences:

5' CCGCACGTTCTCTCAAGCAGGAC 3' and 5'
    GTCTGACGGTTCTTAAGCTGGGAG 3'.

* * * * *

UNITED STATES PATENT AND TRADEMARK OFFICE
CERTIFICATE OF CORRECTION

PATENT NO. : 5,232,829
DATED : August 3, 1993
INVENTOR(S) : Longiaru et al

It is certified that error appears in the above-indentified patent and that said Letters Patent is hereby corrected as shown below:

Column 18, line 10, Claim 3, "Tao" should be --Taq--.
Column 19, line 14, Claim 15, "44" should be --14--.
Column 20, line 6, Claim 16, "trachomatic" should be --trachomatis--.

Signed and Sealed this

Twenty-second Day of August, 1995

*Attest:*

BRUCE LEHMAN

*Attesting Officer*     *Commissioner of Patents and Trademarks*